United States Patent [19]

Seiler et al.

[11] Patent Number: 5,187,291
[45] Date of Patent: Feb. 16, 1993

[54] PROCESS FOR THE SIMULTANEOUS AND CONTINUOUS PREPARATION OF ACYLOXYSILANES AND CARBOXYLIC ACID CHLORIDES

[75] Inventors: Claus-Dietrich Seiler; Reinhold Schork; Albert Frings; Hans-Joachim Kötzsch; Hartwig Rauleder, all of Rheinfelden, Fed. Rep. of Germany

[73] Assignee: Hüls Aktiengesellschaft, Marl, Fed. Rep. of Germany

[21] Appl. No.: 868,548

[22] Filed: Apr. 14, 1992

[30] Foreign Application Priority Data

Apr. 18, 1991 [DE] Fed. Rep. of Germany ....... 4112650

[51] Int. Cl.$^5$ .............................................. C07F 7/08
[52] U.S. Cl. ............................................... 556/442
[58] Field of Search ..................................... 556/442

[56] References Cited

U.S. PATENT DOCUMENTS

| 2,017,000 | 10/1935 | Hintermaier | 556/442 X |
| 2,566,347 | 9/1951 | MacKenzie | 556/442 |
| 3,974,198 | 10/1976 | Ashby | 556/442 |
| 4,329,484 | 5/1982 | Petersen | 556/442 |
| 4,332,956 | 6/1982 | Tolentius | 556/442 |
| 4,556,725 | 12/1985 | Kauner et al. | 556/442 |

*Primary Examiner*—Paul F. Shaver
*Attorney, Agent, or Firm*—Felfe & Lynch

[57] ABSTRACT

Acyloxysilanes and carboxylic acid chlorides can be prepared simultaneously and continuously from organochlorosilanes and monocarboxylic acid anhydrides. Catalytically active amounts of organic bases soluble in the reaction mixture, their salts or organic acid amides are employed here.

13 Claims, 1 Drawing Sheet

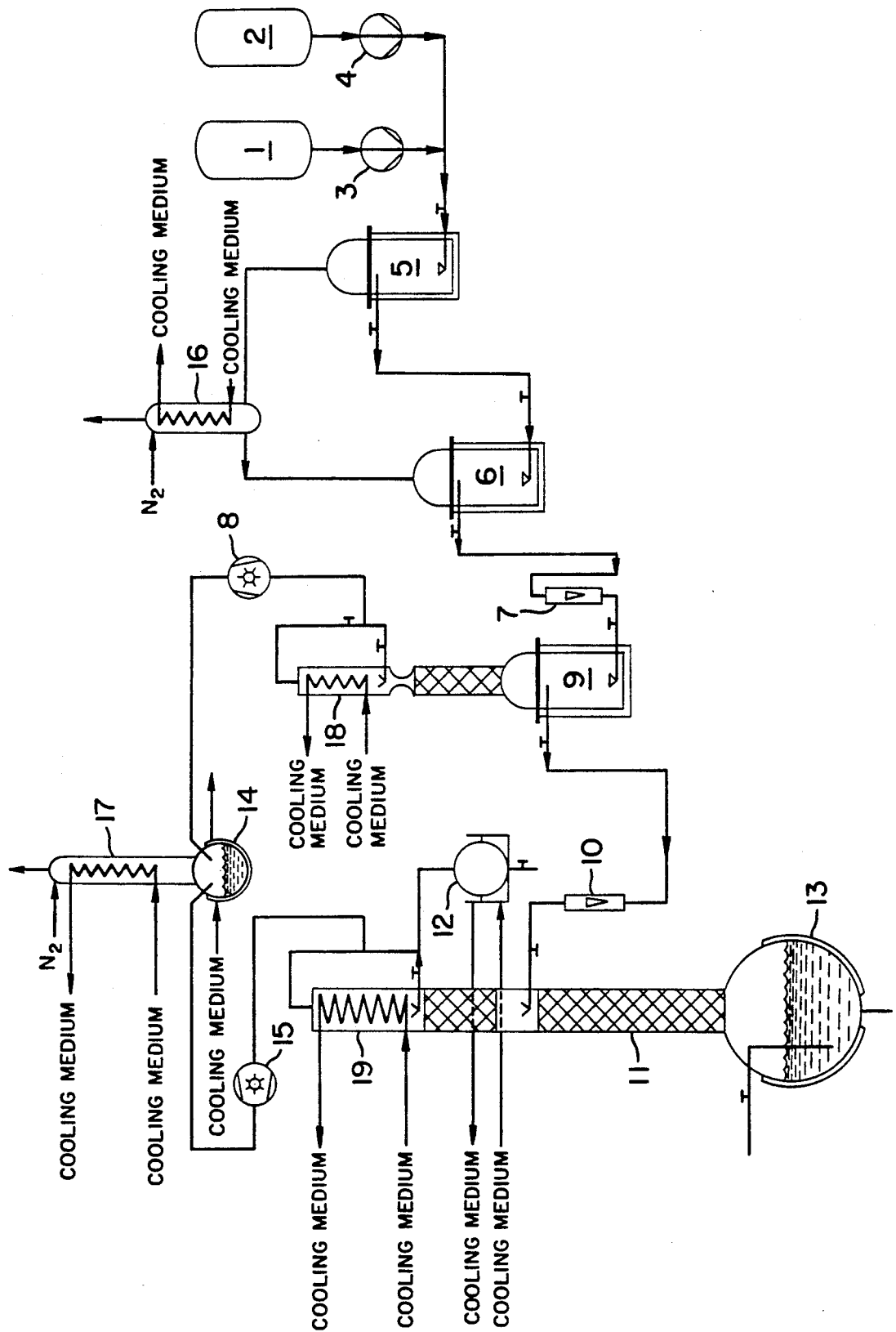

PROCESS FOR THE SIMULTANEOUS AND CONTINUOUS PREPARATION OF ACYLOXYSILANES AND CARBOXYLIC ACID CHLORIDES

FIELD OF THE INVENTION

The present invention relates to a process for the simultaneous and continuous preparation of acyloxysilanes and carboxylic acid chlorides by reaction of organochlorosilanes with monocarboxylic acid anhydrides.

BACKGROUND OF THE INVENTION

Acyloxysilanes have found various uses in the chemical industry. They are suitable, for example, as crosslinking silicon compounds in the preparation of compositions which can be stored in the absence of water and can be hardened to elastomers at room temperature in the presence of moisture. Such compositions are obtained by mixing diorganopolysiloxanes containing end groups which can undergo condensation and crosslinking silicon compounds. Examples of acyloxysilanes which are suitable for this purpose are vinyl-, methyl- and ethyltriacetoxysilanes. Carboxylic acid chlorides are important and, in some cases, valuable raw materials for the synthesis of organic compounds.

It is known that alkanoyloxysilanes can be prepared continuously by reaction of organochlorosilanes with alkanoic acids at elevated temperature in a column (DE-PS 28 01 780). The alkanoic acid is passed in vaporized form from the bottom upwards in countercurrent with the organochlorosilane and reacts to form alkanoyloxysilane and hydrogen chloride.

A disadvantage of this procedure is that the hydrogen chloride formed is in contact with the alkanoic acids employed for relatively long periods of time under conditions under which the formation of water and alkanoyl chlorides takes place. This results in additional siloxane formation and requires expensive low-temperature cooling at the top of the column so that the substances entrained in the stream of hydrogen chloride according to their vapor pressure are deposited and the hydrogen chloride is rendered usable for purposes for which particular purity requirements are imposed. Another disadvantage of this procedure is that metering of the alkanoic acids introduced into the column must be regulated by an expensive device which is controlled by a temperature measurement point in the lower part of the column.

It is also a further disadvantage of the procedure of DE-PS 28 01 780 that the reaction, which is associated with the release of large amounts of gas, must be carried out in vacuo, which necessitates particular pressure stabilization equipment.

Because of the deficiencies associated with the procedure according to DE-PS 28 01 780, ethyltriacetoxysilane is obtained in the distillation column with an ethyltriacetoxysilane content of only 94%, coupled with a content of 2% of acetic acid and evidently 4% of siloxanes, as well as a content of hydrolyzable chlorine of about 50 ppm.

Only a slight improvement to this situation is achieved if in this known procedure the addition of the alkanoic acid together with the organochlorosilane is carried out in the lower part of the column and additional alkanoic acid is introduced in the upper part of the column (DE-PS 32 21 702).

It is also known that the reaction of organochlorosilanes can be carried out with anhydrides corresponding to the alkanoic acids; however, only a discontinuous procedure has been described for this reaction.

There was therefore the problem of discovering a continuous process, which can be used on a large industrial scale, for the preparation of acyloxysilanes which does not have the deficiencies of the procedures according to the prior art described herein, and in which a high-quality by-product in the form of carboxylic acid chloride is obtained instead of the relatively useless by-product hydrogen chloride.

SUMMARY OF THE INVENTION

These problems were solved by developing a process for the simultaneous and continuous preparation of an acyloxysilane and a carboxylic acid chloride by reacting an organochlorosilane with excess monocarboxylic acid anhydride at elevated temperatures, separating off the carboxylic acid chloride after the reaction has ended and subsequently collecting the acyloxysilane, wherein said process is characterized in that the starting components are passed through one or more reactors at temperatures of 25° to 100° C. with the addition of organic bases which are soluble in the reaction mixture, their salts or organic acid amides. The carboxylic acid chloride formed is then removed in vacuo in a distillation reactor and the reaction mixture which remains after the carboxylic acid chloride has been separated off is transferred to the central intake of a column. Excess carboxylic acid anhydride is distilled off at the top of the column in vacuo and the acyloxysilane is removed from the bottom of the distillation column.

DETAILED DESCRIPTION OF THE INVENTION

The chlorosilanes which can be employed as starting substances in the process according to the invention correspond to the general formula

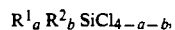

$$R^1_a R^2_b \text{SiCl}_{4-a-b},$$

wherein a can have the value 3, 2 or 1 and b can have the value 1 or 0.

Preferably, a=1 and b=0.

$R^1$ and $R^2$ represent hydrogen or identical or different saturated hydrocarbon radicals of 1 to 10 carbon atoms or unsaturated hydrocarbon radicals of 2 to 10 carbon atoms, which can optionally contain functional groups, for example halogen, which do not undergo a reaction under the reaction conditions described.

The following compounds can thus be employed, for example, as silicon-containing starting substances:

vinyltrichlorosilane,
ethyltrichlorosilane,
methyltrichlorosilane,
trichlorosilane,
propyltrichlorosilane and
2-chloroethyl-methyldichlorosilane.

The carboxylic acid anhydrides employed according to the invention are mainly derived from monobasic aliphatic acids, preferably from those having 2 to 4 carbon atoms. The hydrocarbon radicals of the acid may be saturated or unsaturated. Examples of such anhydrides are ethanoic anhydride, propanoic anhydride and butanoic anhydride. However, compounds in which a hydrogen atom of the aliphatic radical is replaced by a phenyl radical, such as phenylmethanoic anhydride, can also be employed.

The reactor system used in the process according to the invention is a system which, in the simplest case, consists of two reaction vessels connected in series, through which the starting substances flow and in which their residence time can be adjusted to suit the product-specific reaction requirements by an appropriate vessel design. The reactors are advantageously connected such that the reaction mixture formed is removed from the preceding reactor at the top and fed into the subsequent reactor at the bottom. The second reactor is called a distillation reactor and is provided with a column top which is fitted with a reflux divider and condenser and via which the carboxylic acid chlorides formed in the preceding reactor, and still forming in the distillation reactor in the course of removal of the carboxylic acid chlorides by distillation, are removed under a pressure of 5 to 300 mbar. Any desired number of reactors in which the reaction and establishment of the reaction equilibrium take place can be chosen. One reactor is usually sufficient to ensure complete reaction of the starting component used in less than the equivalent amount and that therefore the reaction mixture which leaves the distillation reactor and is passed into the central intake of a column no longer contains the component used in less than the equivalent amount. Preferred reactors in the context of the present invention are tube reactors.

The reactors can be heated, for example, via double-walled jacket systems. It should be made certain here that the reactors can be exposed to various temperature ranges so that the most favorable reaction temperatures for achieving optimum rates of reaction can be established for the particular starting substances. Agitation of the reaction mixture can be established effectively in the distillation reactor, for example by using stirrer systems having an intense action, so that as complete as removal as possible of the carboxylic acid chloride formed, according to the starting components employed, is achieved. If possible, the residual chlorine content in the reaction mixture, which emerges from the distillation reactor and enters the central intake of the distillation column downstream, should not exceed 8,000 ppm. However, chlorine contents slightly in excess of this do not present problems. As a result of a mode of operation adapted to suit these contents of the column downstream of the distillation reactor, it is possible for chlorine contents in the intake which are too high, to be compensated without the slightest reductions being found in the quality of the products leaving the bottom of the distillation column.

It has been found that in order to achieve economical space-time yields, the temperatures used in the reactors should not fall below 25° C. The space-time yield is also reduced if the temperature used in the reactors is in a temperature range in which intermolecular condensation of the acyloxysilanes to give siloxanes is initiated to an increased degree. The temperature range in which intermolecular condensation of the acyloxysilanes starts depends both on the chlorosilane employed and on the acyloxy group which replaces the chlorine in the chlorosilane, so that the optimum reaction temperature must be determined from case to case in preliminary experiments. When the synthesis of most acyloxysilanes is used in practice, there are no differences in respect to the space-time yield if the reaction temperature used in each case in the individual reaction units of the reactor system is kept in the temperature range of 50° to 90° C.

The procedure described thus far for reacting the starting substances of organochlorosilane and monocarboxylic acid anhydride in the reaction units of the reactor system can be carried out with economically acceptable space-time yields only if, in accordance with the present invention, the reaction of the starting substances fed in is carried out in the presence of additives having a catalytic action.

Organic bases, salts thereof and acid amides have proved to be particularly suitable substances having a catalytic action for carrying out the procedure according to the invention.

Primary, secondary and tertiary amines can thus be employed as organic bases. Examples which may be mentioned are the compounds phenylamine, cyclohexylamine, propylamine, isopropylamine, morpholine, piperidine, dicyclohexylamine, triethylamine, triethanolamine, pyridine, benzothiazole, and methylpyrrolidone.

It has been found that secondary and tertiary amines containing different groups in the molecule, for example, methylethylamine and dimethylethylamine, are also active in the context of the present invention. Mixtures of the amines mentioned likewise show a corresponding activity, without positive or negative synergistic effects having been found.

No differences have been found in using salts compared with using the bases themselves in respect to activity in carrying out the reactions according to the invention. The salt form which is preferably employed is hydrochloride. However, hydrobromides and the salts formed with organic acids, such as the propionates, can also be employed without limiting the activity. The salts of the organic bases employed are preferably added to the reaction starting substances in dissolved form, ethanol, for example, being a suitable solvent.

Organic acid amides have proved to be equally effective as the organic bases and salts thereof in accelerating the course of the reaction according to the invention. Examples which may be mentioned are the compounds acetamide, N-methylacetamide, N,N-methylethylpropionamide, benzamide and thiourea.

The acid amides are added in liquid or also in dissolved form. Mixtures of the above acid amides also show a corresponding activity, without synergistic effects being observed here.

The amount of additives to be used can be varied within wide limits. To achieve optimum results the amounts of active substance to be added to the mixture of the starting substances can be 5 to 1,000 ppm. The preferred range is 10 to 100 ppm, based on the particular mixture of the reactants intended for reaction. The use of larger amounts provides no further advantages.

The reaction mixture which has essentially been freed from the corresponding carboxylic acid chlorides passes from the distillation reactor into the central intake of a column used as a distillation column in a manner which is known per se. The column can be operated either under normal pressure or under reduced pressure. The mode of operation of the column is adapted to suit the particular heat stability of the acyloxysilanes prepared. The carboxylic acid chloride is preferably removed from the distillation reactor under a pressure of 5 to 300 mbar. The particularly preferred made of operation comprises operating the column under a pressure of 5 to 25 mbar. With this mode of operation, the boiling range of the carboxylic acid anhydride employed corresponding to the particular column internal pressure is established as the temperature at the top of the column.

As already mentioned, the mode of operation of the column is adapted to suit the heat stability of the acyloxysilanes formed in each case. In other words the operating pressure in the column is chosen so that at the bottom of the distillation column a temperature prevails which is below the temperature at which intermolecular condensation of the acyloxysilane present is detectable.

1.05 to 1.2 mol of carboxylic acid anhydride are preferably employed per gram-atom of silicon-bonded chlorine.

The invention is explained below with the aid of the drawing and the examples.

The drawing shows, schematically, an embodiment of a plant for carrying out the process according to the invention. The starting substances of organochlorosilane and carboxylic acid anhydride together with additives which act as catalysts are fed from storage tanks 1 and 2 via metering pumps 3 and 4 into reactor 5 continuously in a fixed ratio of amounts, and are brought to the reaction temperature in this reactor. The reaction mixture passes from reactor 5 into reactor 6, from which it is passed, metered via rotameter 7, into distillation reactor 9, which is connected to a vacuum system 8. The carboxylic acid chloride formed is removed from the reaction mixture in this reactor, and after passing through vacuum pump 8 collects in cooling reservoir 14. The product which remains, which may still contain small amounts of carboxylic acid chloride and unreacted starting substances, is fed via flowmeter 10 into the central intake of the column 11, filled with saddle packing, of a distillation column connected to a vacuum system 15. Excess carboxylic acid anhydride is removed in the upper part of the column and fed continuously to cooled reservoir 12. The acyloxysilane is removed continuously from the bottom 13 of the distillation column.

EXAMPLE 1 (COMPARISON EXAMPLE)

Preparation of ethyl-tris(ethanoyloxy)silane and ethanoyl chloride

Ethyltrichlorosilane is introduced into reservoir tank 1 and ethanoic anhydride into reservoir 2. 125 g (0.765 mol) of ethyltrichlorosilane per hour and 281 g (2.76 mols) of ethanoic anhydride per hour are fed by means of metering pumps 3 and 4 into the lower part of reactor 5 (volume=1 liter), in which the starting substances are heated to 60° C. After passing through reactor 5, the reaction mixture enters, via condenser 16, reactor 6 (volume=1 liter), in which it is kept at 60° C. and from which it is then fed, via rotameter 7, into distillation reactor 9 (volume=1 liter) in an amount of about 406 g per hour. The reaction mixture is heated to 90° C. in this reactor, and the ethanoyl chloride formed so far and still forming is distilled off from the reaction mixture under a pressure of 50 to 60 mbar (vacuum pump 8) and taken via condenser 18 to cooled reservoir 14. The amount of ethanoyl chloride collected per hour in reservoir 14 is about 172 g (2.2 mols)

The product removed in the upper part of distillation reactor 9 is introduced via rotameter 10 into the central intake of distillation column 11, which consists of a 1.60 m long glass tube of 5 cm diameter and is filled with saddle packing of 6 mm diameter. Condenser 19 at the top of the column and distillate reservoir 12 are charged with a cooling liquid (− 27° C.) A 4 liter double-walled flask 13 heated by a thermostat (circulation temperature about 125° C.) forms the bottom end of the column. The crude product fed in is worked up in the distillation column under an internal column pressure of 5 to 7 mbar at a temperature of about 110° C. at the bottom of the column. Ethyl-tris(ethanoyloxy)silane is constantly removed from the double-walled flask 13, which is half-filled with liquid, at a rate such that the level of liquid in flask 13 remains unchanged. Excess ethanoic anhydride is distilled off in the upper part of the column, and is collected in distillate reservoir 12. The residual ethanoyl chloride is distilled off at the top of the column via condenser 19 and vacuum pump 15 into reservoir 14 provided with condenser 17.

The product removed from the double-walled flask 13 consists of

| | |
|---|---|
| ethyl-tris(ethanoyloxy)silane | about 95.8% by weight |
| ethyl-di(ethanoyloxy)chlorosilane | about 0.37% by weight |
| ethyl-ethanoyloxydichlorosilane | about 0.06% by weight |
| siloxanes | about 1.9% by weight |
| ethanoic anhydride | about 1.8% by weight |
| chlorine, hydrolyzable | about 800 ppm. |
| Yield: 97.5% | |

EXAMPLE 2 (COMPARISON EXAMPLE)

Preparation of methyl-tris(propanoyloxy)silane and propanoyl chloride

The procedure described in Example 1 is repeated, with the following changes being made:

Instead of ethyltrichlorosilane and ethanoic anhydride, methyltrichlorosilane and propanoic anhydride are reacted. Methyltrichlorosilane is fed into the reactor system in an amount of 114 g (0.765 mol) per hour, and propanoic anhydride in an amount of 383 g (2.94 mols) per hour. The amount of propanoyl chloride collected per hour in reservoir 14 is about 212 g (2.29 mols). The product removed from double-walled flask 13 of the distillation column has the following composition:

| | |
|---|---|
| methyl-tris(propanoyloxy)silane | about 96.1% by weight |
| methyl-bis(propanoyloxy)chlorosilane | about 0.32% by weight |
| methyl-propanoyloxydichlorosilane | about 0.05% by weight |
| siloxanes | about 1.7% by weight |
| propanoic anhydride | about 1.8% by weight |
| chlorine, hydrolyzable | 700 ppm. |
| Yield: 96.9% | |

EXAMPLE 3 (COMPARISON EXAMPLE)

Preparation of methylpropyl-bis(ethanoyloxy)silane and ethanoyl chloride

The procedure described in Example 1 is repeated, with the following changes being made:

Instead of ethyltrichlorosilane, methylpropyldichlorosilane is reacted with ethanoic anhydride. Methylpropyldichlorosilane is fed into the reactor system in an amount of 120 g (0.765 mol) per hour, and ethanoic anhydride in an amount of 234 g (2.29 mols) per hour.

The amount of ethanoyl chloride collected per hour in reservoir 14 is about 120 g (1.53 mol).

The product removed from double-walled flask 13 of the column has the following composition:

| | |
|---|---|
| methylpropyl-bis(ethanoyl-oxy(silane) | 96.7% by weight |
| methylpropyl-ethanoyloxy-chlorosilane | 0.7% by weight |
| siloxanes | 1.5% by weight |
| ethanoic anhydride | 1.1% by weight |
| chlorine, hydrolyzable | about 1,180 ppm. |
| Yield: 97.5% | |

EXAMPLE 4

Preparation of ethyl-tris(ethanoyloxy)silane and ethanoyl chloride

The procedure described in Example 1 is repeated, with the following amendments being made:

Instead of 125 g (0.765 mol) of ethyltrichlorosilane and 281 g (2.76 mols) of ethanoic anhydride, 156 g (0.96 mol) of ethyltrichlorosilane and 352 g (3.46 mols) of ethanoic anhydride, to which 51 mg of triethylamine have been added (corresponding to 100 ppm, based on the mixture of the reactants), are used per hour for the feed.

The product removed from double-walled flask 13 consists of:

| | |
|---|---|
| ethyl-tris(ethanoyloxy)-silane | 97.2% by weight |
| ethyl-di(ethanoyloxy)-chlorosilane | — |
| ethyl-ethanoyloxy-dichlorosilane | — |
| siloxanes | 1.7% by weight |
| ethanoic anhydride | 1.1% by weight |
| chlorine, hydrolyzable | 3 ppm. |
| Yield: 97.8% | |

EXAMPLE 5

Preparation of ethyl-tris(ethanoyloxy)silane and ethanoyl chloride

The procedure described in Example 4 is repeated. Instead of 51 mg of triethylamine, an amount of 5.1 mg of triethylamine (corresponding to 10 ppm, based on the mixture of the reactants) is added to the ethanoic anhydride.

The product removed from double-walled flask 13 consists of:

| | |
|---|---|
| ethyl-tris(ethanoyloxy)-silane | 97.2% by weight |
| ethyl-di(ethanoyloxy)-chlorosilane | — |
| ethyl-ethanoyloxy-dichlorosilane | — |
| siloxanes | 1.9% by weight |
| ethanoic anhydride | 0.9% by weight |
| chlorine, hydrolyzable | 5 ppm. |
| Yield: 97.6% | |

EXAMPLES 6 TO 9

Preparation of ethyl-tris(ethanoyloxy)silane and ethanoyl chloride

The procedure described in Example 4 is repeated. Instead of 51 mg of triethylamine, an amount of
25 mg of phenylamine or
25 mg of cyclohexylamine or
25 mg of n-propylamine or
25 mg of isopropylamine
(corresponding to 50 ppm, based on the mixture of the reactants) is added to the ethanoic anhydride.

The products removed from double-walled flask 13 have the following composition range:

| | |
|---|---|
| ethyl-tris(ethanoyloxy)-silane | 97.2 to 97.4% by weight |
| ethyl-di(ethanoyloxy)-chlorosilane | — |
| ethyl-ethanoyloxy-dichlorosilane | — |
| siloxanes | 1.9 to 2.0% by weight |
| ethanoic anhydride | 0.6 to 0.9% by weight |
| chlorine, hydrolyzable | 2 to 7 ppm. |
| Yield: 97.2 to 97.4%. | |

EXAMPLES 10 TO 12

Preparation of ethyl-tris(ethanoyloxy)silane and ethanoyl chloride

The procedure described in Example 4 is repeated. Instead of 51 mg of triethylamine, an amount of
18 mg of diethylamine or
18 mg of dicyclohexylamine or
18 mg of piperidine
(corresponding to 35 ppm, based on the mixture of the reactants) is added to the ethanoic anhydride.

The products removed from double-walled flask 13 have the following composition range:

| | |
|---|---|
| ethyl-tris(ethanoyloxy)-silane | 97.0 to 97.3% by weight |
| ethyl-di(ethanoyloxy)-chlorosilane | — |
| ethyl-ethanoyloxy-dichlorosilane | — |
| siloxanes | 1.6 to 2.3% by weight |
| ethanoic anhydride | 0.7 to 1.1% by weight |
| chlorine, hydrolyzable | 2 to 5 ppm. |
| Yield: 97.1 to 97.9%. | |

EXAMPLES 13 TO 15

Preparation of ethyl-tris(ethanoyloxy)silane and ethanoyl chloride

The procedure described in Example 4 is repeated. Instead of 51 mg of triethylamine, an amount of
34 mg of pyridine or
34 mg of benzothiazole or
34 mg of methylpyrrolidone
(corresponding to 65 ppm, based on the mixture of the reactants) is added to the ethanoic anhydride.

The products removed from double-walled flask 13 have the following composition range:

| | |
|---|---|
| ethyl-tris(ethanoyloxy)-silane | 96.5 to 97.4% by weight |
| ethyl-di(ethanoyloxy)- | — |

-continued

| | |
|---|---|
| chlorosilane | |
| ethyl-ethanoyloxy-dichlorosilane | — |
| siloxanes | 2.1 to 2.4% by weight |
| ethanoic anhydride | 0.7 to 1.1% by weight |
| chlorine, hydrolyzable | 3 to 7 ppm. |
| Yield: 96.8 to 97.4%. | |

EXAMPLE 16

Preparation of ethyl-tris(ethanoyloxy)silane and ethanoyl chloride

The procedure described in Example 4 is repeated. Instead of 51 mg of triethylamine, an amount of 52 mg of triethylamine hydrochloride (dissolved in ethanol, corresponding to 50 ppm, based on the mixture of the reactants) is added to the ethanoic anhydride.

The product removed from double-walled flask 13 has the following composition:

| | |
|---|---|
| ethyl-tris(ethanoyloxy)-silane | 97.6% by weight |
| ethyl-di(ethanoyloxy)-chlorosilane | — |
| ethyl-ethanoyloxy-dichlorosilane | — |
| siloxanes | 1.6% by weight |
| ethanoic anhydride | 0.8% by weight |
| chlorine, hydrolyzable | 3 ppm. |
| Yield: 97.9% | |

EXAMPLES 17 TO 19

Preparation of ethyl-tris(ethanoyloxy)silane and ethanoyl chloride

The procedure described in Example 4 is repeated. Instead of 51 mg of triethylamine, an amount of
- 50 mg of acetamide (dissolved in ethanol) or
- 25 mg of N,N-methylethylacetamide or
- 12 mg of thiourea (dissolved in ethanoic acid)

(corresponding to 100 ppm or 50 ppm or 25 ppm, respectively, based on the mixture of the reactants) is added to the ethanoic anhydride.

The products removed from double-walled flask 13 have the following composition range:

| | |
|---|---|
| ethyl-tris(ethanoyloxy)-silane | 97.0 to 97.2% by weight |
| ethyl-di(ethanoyloxy)-chlorosilane | — |
| ethyl-ethanoyloxy-dichlorosilane | — |
| siloxanes | 1.6 to 2.1% by weight |
| ethanoic anhydride | 0.9 to 1.2% by weight |
| chlorine, hydrolyzable | 5 ppm. |
| Yield: 97.4 to 97.8%. | |

EXAMPLES 20 TO 24

Preparation of methylpropyl-bis(ethanoyloxy)silane and ethanoyl chloride

The procedure described in Example 3 is repeated, the following changes being made:

Instead of 120 g (0.765 mol) of methylpropyldichlorosilane and 234 g (2.29 mols) of ethanoic anhydride, 150 g (0.96 mol) of methyl propyldichlorosilane and 230 g (2.25 mols) of ethanoic anhydride, to which an amount of
- 30 mg of n-propylamine or
- 30 mg of diethylamine or
- 30 mg of benzothiazole or
- 30 mg of triethylamine hydrochloride (dissolved in ethanol) or
- 30 mg of acetamide is added (corresponding to 75 ppm, based on the mixture of the reactants), are fed into the reactor system per hour. The products removed from double-walled flask 13 have the following composition range:

| | |
|---|---|
| methylpropyl-bis(ethanoyloxy)silane | 97.1 to 97.4% by weight |
| methylpropyl-ethanoyloxy-chlorosilane | — |
| siloxanes | 1.6 to 2.2% by weight |
| ethanoic anhydride | 0.7 to 1.0% by weight |
| chlorine, hydrolyzable | 5 to 7 ppm. |
| Yield: 97.0 to 97.9%. | |

EXAMPLE 25

Preparation of vinyl-tris(propanoyloxy)silane and propanoyl chloride

The procedure described in Example 2 is repeated, the following changes being made:

Instead of 114 g (0.765 mol) of methyltrichlorosilane and 383 g (2.94 mols) of propanoic anhydride, 156 g (0.956 mol) of vinyltrichlorosilane and 440 g (3.38 mols) of propanoic anhydride, to which 30 mg of methylethylamine and 30 mg of ethylamine have been added, are fed into the reactor system per hour.

The product removed from double-walled flask 13 has the following composition:

| | |
|---|---|
| vinyl-tris(propanoyloxy)-silane | 97.3% by weight |
| vinyl-bis(propanoyloxy)-chlorosilane | — |
| vinyl-propanoyloxy-dichlorosilane | — |
| siloxanes | 1.8% by weight |
| propanoic anhydride | 0.9% by weight |
| chlorine, hydrolyzable | 9 ppm. |
| Yield: 97.7%. | |

EXAMPLE 26

Preparation of 2-chloroethylmethyl-bis-(ethanoyloxy)silane and ethanoyl chloride The procedure described in Example 4 is repeated. Instead of 156 g (0.96 mol) of ethyltrichlorosilane and 352 g (3.46 mols) of ethanoic anhydride, to which 51 mg of triethylamine have been added, 255 g (1.44 mols) of 2-chloroethylmethyldichlorosilane and 346 g (3.40 mols) of ethanoic anhydride, to which 51 mg of triethylamine have been added, are used per hour for the feed into the reactors. The product removed from double-walled flask 13 has the following composition:

| | |
|---|---|
| 2-chloroethylmethyl-bis-(ethanoyloxy)silane | 97.2% by weight |
| 2-chloroethylmethyl-ethanoyloxy-chlorosilane | — |
| siloxanes | 1.8% by weight |

| | |
|---|---|
| ethanoic anhydride | 1.0% by weight |
| chlorine, hydrolyzable | 10 ppm. |
| Yield: 97.6% | |

It will be understood that the specification and examples are illustrative but not limitative of the present invention and that other embodiments within the spirit and scope of the invention will suggest themselves to those skilled in the art.

We claim:

1. Process for the simultaneous and continuous preparation of acyloxysilane and carboxylic acid chloride comprising reacting an organochlorosilane with excess monocarboxylic acid anhydride at an elevated temperature, separating the carboxylic acid chloride when said reaction has ended and collecting the acyloxysilane, wherein said organochlorosilane and monocarboxylic acid anhydride are passed through at least one reactor at a temperature of 25° to 100° C. with the addition of organic bases, their salts or organic acid amides which are soluble in said reaction mixture, removing said carboxylic acid chloride in vacuo in a distillation reactor and transferring said reaction mixture which remains after said carboxylic acid chloride has been separated off to a central intake of a distillation column, said excess carboxylic acid anhydride being distilled off at the top of said distillation column in vacuo and said acyloxysilane being removed from said distillation column.

2. Process according to claim 1, wherein said organic bases are selected from the group consisting of tertiary, secondary and primary amines.

3. Process according to claim 1, wherein the organic salts are selected from the group consisting of tertiary, secondary and primary amines.

4. Process according to claim 1, wherein the organic acid amides are unsubstituted, N-substituted acid amides or mixtures thereof.

5. Process according to claim 2, wherein dialkylamines, trialkylamines or mixtures thereof are added.

6. Process according to claim 3, wherein dialkylamine hydrochlorides, trialkylamine hydrochlorides or mixtures thereof are added.

7. Process according to claim 4, wherein mono- or dialkylsubstituted carboxylic acid amides are added.

8. Process according to claim 1, wherein from 5 to 1,000 ppm of said organic bases, salts thereof or their organic acid amides are added.

9. Process according to claim 8, wherein said organic bases, salts thereof or the organic acid amides are employed in amounts of 10 to 100 ppm.

10. Process according to claim 1, wherein the maximum reaction temperature in the reactors is below the temperature at which intermolecular condensation of the acyloxysilane formed is detectable.

11. Process according to claim 10, wherein the reaction temperature in the reactors is 50° to 90° C.

12. Process according to claim 1, wherein the concentration of carboxylic acid anhydride is 1.05 to 1.2 mol per gram-atom of silicon-bonded chlorine.

13. Process according to claim 1, wherein the carboxylic acid chloride is removed from a distillation reactor under a pressure of 5 to 300 mbar.

* * * * *